(12) United States Patent
Radovic

(10) Patent No.: US 10,869,914 B2
(45) Date of Patent: *Dec. 22, 2020

(54) METHODS OF TREATING ABNORMALITIES OF THE FIRST METATARSOPHALANGEAL JOINT OF THE FOOT

(71) Applicant: Philip Andrew Radovic, San Clemente, CA (US)

(72) Inventor: Philip Andrew Radovic, San Clemente, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/734,251

(22) Filed: Jan. 3, 2020

(65) Prior Publication Data

US 2020/0138918 A1    May 7, 2020

Related U.S. Application Data

(63) Continuation of application No. 16/178,334, filed on Nov. 1, 2018, now Pat. No. 10,525,112, which is a continuation of application No. 15/917,492, filed on Mar. 9, 2018, now Pat. No. 10,159,723.

(60) Provisional application No. 62/470,762, filed on Mar. 13, 2017, provisional application No. 62/473,217, filed on Mar. 17, 2017, provisional application No. 62/619,630, filed on Jan. 19, 2018.

(51) Int. Cl.
| | |
|---|---|
| *C12Q 1/14* | (2006.01) |
| *A61K 38/48* | (2006.01) |
| *A61K 9/00* | (2006.01) |
| *A61K 39/08* | (2006.01) |

(52) U.S. Cl.
CPC ........ *A61K 38/4893* (2013.01); *A61K 9/0019* (2013.01); *A61K 39/08* (2013.01)

(58) Field of Classification Search
None
See application file for complete search history.

(56) References Cited

U.S. PATENT DOCUMENTS

| | | | |
|---|---|---|---|
| 7,396,821 B1 | 7/2008 | Wolff | |
| 10,159,723 B2* | 12/2018 | Radovic | ............... A61K 9/0019 |
| 10,525,112 B2* | 1/2020 | Radovic | ............. A61K 38/4893 |
| 2005/0202047 A1 | 9/2005 | Radovic | |
| 2007/0128226 A1 | 6/2007 | Radovic | |
| 2009/0326607 A1 | 12/2009 | Castel | |
| 2018/0256689 A1 | 9/2018 | Radovic | |
| 2019/0070273 A1 | 3/2019 | Radovic | |

FOREIGN PATENT DOCUMENTS

| | | |
|---|---|---|
| JP | 2007-513964 A | 5/2007 |
| WO | WO 2005/079828 A2 | 9/2005 |

OTHER PUBLICATIONS

Chang Gung Memorial Hospital, Effect of Botulinum to Hallux Valgus in Addition to Total Contact Insole, ClinicalTrials.gov Identifier NCT01501500; Dec. 29, 2011; 6 pages.
Chen et al., Effective Conservative Treatment for Managing Painful Hallux Valgus, Medical Research Archives, vol. 4, Issue 5, 2016.
International Search Report & Written Opinion, dated Jun. 27, 2018 in international Application No. PCT/US2018021860.
Moghtaderi et al., Evaluation of the Therapeutic Effect of Botulinum toxin A on Hallux Valgus Deformity and Pain, 2017.
Saitou et al., Innervation zones of the upper and lower limb muscles estimated by using multichannel surface EMG, Journal of Human Ergology, vol. 29, pp. 35-52, 2000.
Swathi, G.G.N., et al., Morphology and neurovascular supply of extensor digitorum brevis muscle of the foot in humans: Implications for reconstructive surgeries, Indian Journal of Clinical Anatomy and Physiology, vol. 4, No. 1, pp. 106-111, 2017.
Wu et al., Botulinum Toxin Type A Injections for Patients With Painful Hallux Valgus: A 2 Double-Blind, Randomized Controlled Study; Clinical Neurology and Neurosurgery, vol. 129, No. S1, pp. s58-s62, 2015.
Radovic et al., Nonsurgical Treatment for Hallux Abducto Valgus with Botulinum Toxin A, Journal of the American Podiatric Medical Association, vol. 98, No. 1, pp. 61-65, 2008.
Radovic, P.A., Nonsurgical Treatment for Hallux Abducto Valgus with Botulinum Toxin Type A, J. Am. Podiatr. Med. Assoc., vol. 110, No. 2, pp. 1-9, 2020.

\* cited by examiner

*Primary Examiner* — Jennifer E Graser
(74) *Attorney, Agent, or Firm* — Knobbe, Martens, Olson & Bear, LLP

(57) ABSTRACT

A method for treating an abnormality of the first metatarsophalangeal joint of the foot of a mammal includes electrically stimulating a site on each of the extensor hallucis brevis and adductor hallucis muscles of a foot of the mammal affected by the abnormality, and visually confirming that the stimulated muscles responds to the stimulation by contracting. An amount of botulinum toxin effective to treat the abnormality is then injected to the confirmed sites on the extensor hallucis brevis and the adductor hallucis muscles of the affected foot.

8 Claims, 11 Drawing Sheets

- Left - Pre-injection A
- Right - Pre-injection B

- Left - 21 days post-injection A
- Right - 21 days post-injection B

- Left - 42 days post-injection A and 21 days post-injection B
- Right - 42 days post-injection B and 21 days post-injection A RIGHT FOOT
• Pre-injection A RIGHT FOOT
- 27 days post-injection A RIGHT FOOT
- 43 days post-injection A RIGHT FOOT
- 63 days post-injection A LEFT FOOT
- Pre-injection A+B+C LEFT FOOT
- 21 days post-injection A+B+C LEFT FOOT
- 35 days post-injection A+B+C LEFT FOOT
- 63 days post-injection A+B+C

METHODS OF TREATING ABNORMALITIES OF THE FIRST METATARSOPHALANGEAL JOINT OF THE FOOT

PRIORITY AND CROSS REFERENCE TO RELATED APPLICATIONS

This application is a Continuation Application of U.S. application Ser. No. 16/178,334, filed Nov. 1, 2018, and issued as U.S. Pat. No. 10,525,112 on Jan. 7, 2020, which is a Continuation Application of U.S. application Ser. No. 15/917,492, filed on Mar. 9, 2018, and issued as U.S. Pat. No. 10,159,723 on Dec. 25, 2018, which claims priority from U.S. Provisional Patent Application No. 62/470,762, filed on Mar. 13, 2017, U.S. Provisional Patent Application No. 62/473,217, filed on Mar. 17, 2017, and U.S. Provisional Patent Application No. 62/619,630, filed on Jan. 19, 2018, the disclosures of which are incorporated herein by reference. The subject matter of this application also relates to the subject matter of U.S. Pat. No. 7,276,244, which is also hereby incorporated in its entirety.

BACKGROUND

Field of the Disclosure

The present disclosure relates to methods of treating abnormalities of the first metatarsophalangeal joint of the foot.

Description of the Related Art

Abnormalities of the first metatarsophalangeal joint encompass a variety of disorders, including hallux abductovalgus (commonly known as "bunions"), hallux varus, hallux limitus, hallux rigidus, and other disorders.

Hallux abductovalgus ("hallux abductovalgus") is one of the most frequently seen abnormalities of the first metatarsophalangeal joint. In a patient suffering from hallux abductovalgus, the proximal phalanx of the hallux (the great toe) points toward the second toe. This results in a lateral deviation of the great toe (tilting of the great toe away from the mid-line of the body) and a widening of the angle between the first and second metatarsals.

One of the greatest deforming forces in the development of hallux abductovalgus is the Adductor Hallucis (AdH) muscle. This muscle has two muscle bellies, a transverse and an oblique. In a patient with hallux abductovalgus, the adductor hallucis muscle gains mechanical advantage, pulling the hallux laterally and forcing the metatarsal head medially.

The severity of hallux abductovalgus deformities has traditionally been quantified based on a variety of measurements from radiographs. One common measurement is the intermetatarsal angle between the line of the first and second metatarsal. Normally, this angle can average from about 6 to about 8 degrees. In a patient with abductovalgus, the intermetatarsal angle is increased, with severe abnormalities measuring greater than 30 degrees. Another common measurement is the hallux abductus angle, which is the angle between the longitudinal axes of the first metatarsal and the great toe. Normally, this angle can average from about 10 to about 15 degrees. In hallux abductovalgus, the hallux abductus angle is increased, with extreme cases measuring greater than 70 degrees. A third common measurement is the tibial sesamoid position. With hallux abductovalgus, the first metatarsal deviates medially off of the sesamoids, causing apparent lateral dislocation. The position of the tibial sesamoid in relation to a line drawn through the mid-longitudinal axis of the first metatarsal determines the tibial sesamoid position.

Hallux varus is an abnormality of the first metatarsophalangeal joint in which the proximal phalanx of the hallux (great toe) points away from the second toe. This results in a medial deviation of the great toe (tilting of the great toe toward the mid-line of the body). A common deforming force in the development of hallux varus is the abductor hallucis muscle. In a patient with hallux varus, the abductor hallucis muscle can gain mechanical advantage, pulling the hallux medially and forcing the metatarsal head laterally.

Hallux limitus is an abnormality of the first metatarsophalangeal joint that results in a restricted range of motion in the first metatarsophalangeal joint. Normally, the range of motion in the first metatarsophalangeal joint can average from about 55 to about 75 degrees. In a patient with hallux limitus, this range of motion is decreased. When the range of motion becomes less than about 5 degrees, this condition is commonly referred to as hallux rigidus (stiff great toe).

Hallux limitus can be functional or structural. Functional hallux limitus exhibits a restricted range of motion in the first metatarsophalangeal joint only during weight bearing. Structural hallux limitus, on the other hand, exhibits a restricted range of motion in the first metatarsophalangeal joint both during weight bearing and non-weight bearing.

U.S. Pat. No. 7,276,244 proposed treatment of abnormalities of the foot by intramuscular injection of botulinum toxin to the adductor hallucis muscle of the affected foot.

SUMMARY

In embodiments described herein, a method for treating abnormalities of the first metatarsophalangeal joint of the foot of a mammal comprising administering an amount of neuromuscular toxin sufficient to alleviate a symptom of the joint abnormality is improved by being conducted in combination with any of the following:

1. Ultrasonic guided injection
2. Selective injection into specific fascicles/components, including three individual fascicles/components of the oblique head of the adductor hallucis, medial, central and lateral components. Each can be individually injected under Ultrasound (US) guided electrical stimulation. Selective injection into the transverse head can also be conducted. In certain embodiments, three fascicles of the transverse head can also be selected for specific injection under ultrasonic guidance.
3. Prior to injection, the areas for injection can be stimulated systematically to ascertain the most effective areas of end plate clusters for that fascicle. The three areas for the oblique head can be stimulated moving distal to proximal and the area for the transverse head can be stimulated moving medial to lateral.
4. Ultrasound enhanced contrast can also be employed, such as by combining gas bubbles combined with the toxin or by muscle receptor binding ligand combined with toxin.
5. A dynometer can be used on the hallux to quantify the strength of the stimulus at each level (adduction of the hallux towards the second toe).
6. Injecting the extensor hallucis brevis muscle which in many cases is a contributing adductor of the hallux (relative to the 2nd metatarsal).
7. Aspirating can be conducted so as to avoid injection of the toxin into the artery of the first inner-space.

8. Application of a bunion splint or an abductor hallucis muscle stimulator can be employed.

In another embodiment, a method for treating abnormalities of the first metatarsophalangeal joint of the foot of a mammal is provided. The method includes administering an amount of neuromuscular toxin effective to treat said abnormalities via muscular injection to a subject in need thereof to the extensor hallucis brevis muscle of the affected foot.

In another embodiment, the neuromuscular toxin is also injected into the adductor hallucis muscle.

In another embodiment, the neuromuscular toxin is injected into both oblique and transverse heads of the adductor hallucis muscle.

In another embodiment, the neuromuscular toxin is also injected into a lateral head of flexor hallucis brevis muscle.

In another embodiment, the method further includes at least one of the following: ultrasonic guided injection, selective injection into specific fascicles, prior to injection, systematically stimulating areas for injection to ascertain the most effective areas of end plate clusters for a respective fascicle, ultrasound enhanced contrast by combining gas bubbles with the toxin or by combining muscle receptor binding ligand combined with toxin, quantifying via a dynometer on the hallux strength of the stimulus at each level, aspirating so as to avoid injection of the toxin into the artery of a first inner-space of the artery, and applying a bunion splint or an abductor hallucis muscle stimulator.

In another embodiment, the specific fascicles include three individual fascicles of the oblique head of the adductor hallucis, medial, central and lateral components, wherein each can be individually injected under ultrasound guided electrical stimulation.

In another embodiment, the selective injection is conducted on the transverse head.

In another embodiment, the specific fascicles includes three fascicles of the transverse head of the adductor hallucis, medial, central and lateral components, wherein each can be individually injected under ultrasound guided electrical stimulation.

In another embodiment, the oblique head is stimulated moving distal to proximal and the transverse head is stimulated moving medial to lateral.

DETAILED DESCRIPTION

Figure 1:
FIG. 1 is a radiograph of the left and right feet of the patient receiving the treatment described in Example 3. The radiograph illustrates the left foot prior to receiving INJECTION A and the right foot prior to receiving INJECTION B.

U.S. Pat. No. 7,276,244 relates to methods of treating abnormalities of the first metatarsophalangeal joint through the use of neuromuscular toxins. Practice of the invention disclosed in U.S. Pat. No. 7,276,244 involves administering to the patient an amount of toxin sufficient to alleviate a symptom of the joint abnormality. In preferred aspects of that invention, the toxin can be administered by intramuscular injection. Injection of small doses of neuromuscular toxin into the muscle induces an effect similar to denervation, resulting in dose-dependent loss of muscle tone and subsequent muscle atrophy.

The toxin can be any neuromuscular toxin capable of interfering with the connection between muscle and nerve. In preferred aspects, the toxin is an inhibitor of acetylcholine release, such as botulinum toxin or a protein that mimics its acetylcholine release inhibiting effect. Currently, there are seven known serotypes of botulinum toxin, designated as types A through G. Other potentially useful toxins include, but are not limited to, tetanus toxins, tetrodotoxin, difficile toxins, butyricum toxins, and various animal venoms. Staphylococcal alpha-toxin can also be used, as it has also been shown to induce reversible, flaccid paralysis of skeletal muscle. (Harshman, et al., Infect. Immun., 62:421-425, 1994).

Recombinant, synthetic, and derivative neuromuscular toxins can also be used. For example, proteins produced using recombinant DNA technology which mimics the effects of these natural toxins can be used. Suitable toxins can also include proteins synthetically produced using in vitro protein synthesizing techniques well known in the art. Synthetically produced neurotoxins are also intended to include substances which have been rendered neurotoxic by a variety of manipulations, such as enzymatic or chemical processing and conjugation or derivatization with moieties which themselves are neurotoxic. Accordingly, toxins for use in connection with some embodiments include derivatives of naturally occurring toxins and other known toxins. "Derivative" means a chemical entity which is slightly different from a parent chemical entity but which still has a biological effect similar, or substantially similar, to the biological effect of the chemical entity. For example, suitable toxin derivatives can include neurotoxin components that have modified amino acid side chains, as is well known in the art.

It is also contemplated, that embodiments make use of derivatives in the form of fragments, subunits, and chimeras of neuromuscular toxins can be used. Botulinum toxin, for example, is composed of a heavy chain and a light chain, joined together by two disulfide bonds. Through disruption of the disulfide bond, the subunits can be separated and combined with other moieties, such as stabilizers or toxicity enhancers. If re-associated with other subunits or toxic substances, a biologically active chimera suitable for use in the embodiments can be produced. Toxin fragments, e.g., a portion(s) of neurotoxin that retains neurotoxic and/or biological activity, can also be used.

Neurotoxic substances that share amino acid sequence homologies and/or identities with currently known neuromuscular toxins can also be used. In addition, mixtures of toxins can also be used, preferably where such mixtures have been selected to cause longer-lasting action than with a single toxin.

The currently preferred toxin is a botulinum toxin, most preferably botulinum toxin type A. Commercially available from Allergan (BOTOX) and Ipsen (DYSPORT), botulinum toxin type A is an artificially produced neuromuscular paralyzing agent that is currently licensed by the FDA for cervical dystonia, blepharospasm, strabismus, and wrinkles. When injected into muscle, the botulinum toxin binds to the nerve ending and blocks the nerve from releasing acetylcholine. As a result, the muscle cannot contract and effectively relaxes. Botulinum toxin type B is commercially available under the trademark MYOBLOC and has also been shown to be clinically safe and effective in treating a number of neuromuscular conditions. Use of botulinum toxin type F is also being investigated for commercialization.

The degree of muscle relaxation can be regulated by variation of dosage, variation in the method or site of administration, and frequency of administration.

The dose of toxin administered to the patient will depend upon the severity of the condition (e.g. the size of the area requiring treatment, the age and size of the patient and the potency of the toxin). One unit (U) of toxin is defined as the $LD_{50}$ upon intraperitoneal injection into female Swiss Webster mice weighing 18 to 20 grams each. Typically, the dose administered to the patient may be from about 1 to about 1000 units. In one embodiment, the currently preferred dosage for botulinum toxin type A is from about 50 units to about 300 units. Although such a maximum far exceeds the dosage employed in the treatment of blepharospasms and dystonias (10-150 U), it is well below the lethal dose for humans (estimated to be about 3000 U). Most preferably, the range of dosage of botulinum toxin type A is from about 75 units to about 100 units. Those of ordinary skill in the art will know of or can readily determine without undue experimentation suitable dosages for other neuromuscular toxins.

Because the effects of neuromuscular toxins can be delayed, it is further contemplated that post procedural monitoring of the patient can be used to determine if further administration of the toxin is needed. For example, in the case of Hallux abductovalgus, comparison of pre and post procedural measurements of the intermetatarsal angle, the hallux abductus angle, and/or the tibial sesamoid position can be used to determine whether further treatment is required. In a currently preferred aspect of this embodiment, such post procedural monitoring of the patient can be performed at about 3 to 6 weeks following the initial procedure. If such monitoring reveals that further treatment is required, toxin can be readministered as needed.

The effects of botulinum toxin A generally last for about 3 to about 6 months, depending on the patient. If symptoms recur, toxin can be readministered as needed. Frequency of administration for other neuromuscular toxins can be determined using routine experimentation by those skilled in the art.

As described above, the preferred method of administering the selected toxin is by injection into the target muscle. Intramuscular injection can be accomplished using any suitable injection device. For example, a 27-gauge needle in a 3-cc tuberculin syringe can be used to deliver the toxin directly into the muscle. Needle-less injection systems can also be used to inject the toxin into the target muscle.

Alternatively, those of ordinary skill in the art will be able to determine other suitable techniques for administering the toxin. For example, transdermal delivery systems can be used to administer the toxin as needed. In addition, the toxin can be administered during surgery on the foot, in which case any suitable technique for delivering the toxin to the target area during surgery can be used.

If administered by intramuscular injection, those of ordinary skill in the art will be able to determine suitable techniques for injecting the toxin. In currently preferred aspects of this embodiment, electrical stimulation can be used to determine the optimal sites for injection. For example, an injectable needle attached to an electrode can be inserted through the skin and into the target muscle. This needle electrode can then be attached to the stimulator probe of a standard electrical stimulation unit. As the needle is advanced into the muscle, electrical stimulation is delivered to elicit a motor response. As the stimulated muscle responds by contracting, visual identification can be used to confirm that the needle is properly located in the target muscle.

For example, if toxin is to be administered by intramuscular injection to treat hallux varus, the abductor hallucis muscle preferably can be palpated at the medial aspect of the foot and the needle electrode placed from the medial skin directed into the mid belly of the abductor hallucis muscle. Once a motor response is elicited (hallux adduction), the toxin can be injected.

Those of ordinary skill in the art will know of, or can readily ascertain, other suitable techniques for injecting the toxin, if intramuscular injection is to be used. For example, depending on the muscle to be injected, electromyography can be used, alone or in combination with electrical stimulation, to determine the optimal sites for injection. Alternatively, those of ordinary skill in the art may be able to determine the optimal sites of injection anatomically. In addition, those of ordinary skill will appreciate that in some cases there may be reasons to administer the toxin to suboptimal sites. In each case, this process can be repeated as necessary to deliver sufficient toxin to the target area.

In another embodiment, the method optionally further comprises stimulating the muscle opposed to the muscle to which the toxin is administered. In most cases, such further stimulation is unnecessary. When used, stimulation of the opposing muscle can be achieved by using a standard electric muscle stimulator to deliver electronic impulses to the opposing muscle. For example, in the case of hallux abductovalgus, stimulation can be applied by placing electrode pads preferably over the motor points of the abductor hallucis and delivering low volt stimulation to cause a muscle contraction. Most preferably, stimulation of the opposing muscle can be performed by the patient as needed following administration of the neuromuscular toxin. For example, in currently preferred aspects of this embodiment, the patient can be instructed to stimulate the opposing muscle on a daily basis before coming in for follow-up.

In another embodiment, the method optionally further comprises immobilizing the foot to maintain position after the toxin has been administered. The use of immobilization to maintain position following corrective procedures for abnormalities of the first metatarsophalangeal joint is well known in the art. For example, a splint, surgical shoe, ridged sole shoe, casting, gauze, tape, or the like can be used to immobilize to foot following administration of the toxin. In a currently preferred aspect of this embodiment, a standard splint can be placed on the foot after the toxin has been administered. For example, in the case of hallux abductovalgus, the patient preferably can be instructed to place the foot in a bunion splint on a nightly basis before coming in for follow-up.

In another embodiment, immobilization can be used in conjunction with electrical stimulation of the opposing muscle. For example, in the case of hallux abductovalgus, the patient preferably can be instructed to stimulate the abductor hallucis muscle while placing the foot in a bunion splint on a daily basis before coming in for follow-up.

In another embodiment, the toxin can be administered to the patient during surgery on the patient's foot. In preferred aspects, toxin can be administered to the target muscle during surgery for the joint abnormality, preferably after the primary surgical treatment has been carried out. For example, in the case of hallux abductovalgus, the toxin preferably can be administered by intramuscular injection into the adductor hallucis muscle during surgery on the first metatarsophalangeal joint, preferably after the primary surgical treatment has been carried out.

There is provided herein, in several embodiments, methods of treating abnormalities of the first metatarsophalangeal joint of the foot. Non-limiting examples of abnormalities of the first metatarsophalangeal joint of the foot treated by the methods provided herein include, but are not limited to hallux abductovalgus ("bunions", "hallux valgus"), hallux varus, hallux limitus, sesamoid disorders, hallux rigidus. functional hallux limitus, structural hallux limitus, and hallux-sesamoid arthritis. In various embodiments, the abnormalities of the first metatarsophalangeal joint are due to one or more of unstable metatarsophalangeal joint surfaces, oblique joint surfaces located at the proximal first metatarsal joint, flat feet and/or wearing of ill-fitting shoes. In some embodiments, abnormalities of the first metatarsophalangeal joint of the foot comprise one or more of an intermetatarsal angle between the line of the first and second metatarsal of greater than about 6 degrees, a hallux abductus angle greater than about 15 degrees, and/or a tibial sesamoid position of greater than about 0.

In some embodiments, the methods of treating abnormalities of the first metatarsophalangeal joint of the foot comprise administering one or more neuromuscular toxins to one or more muscles of the foot in an amount effective to treat said abnormalities. In some embodiments, the neuromuscular toxin administration is intramuscular injection. In some embodiments, the neuromuscular toxin administration comprises the use of a needle-less injection systems. In still further embodiments, the neuromuscular toxin administration comprises the use of transdermal delivery systems.

Depending on the embodiment, a variety of different muscles of the affected foot are administered the neuromuscular toxins contemplated herein. In some embodiments, the neuromuscular toxin is injected into the extensor hallucis brevis muscle of the affected foot. In some embodiments, the neuromuscular toxin is injected into the flexor hallucis brevis muscle of the affected foot. In some embodiments, the neuromuscular toxin is injected into the adductor hallucis muscle of the affected foot. In some embodiments, the neuromuscular toxin is injected into the extensor hallucis brevis muscle and the flexor hallucis brevis muscle of the affected foot. In some embodiments, the neuromuscular toxin is injected into the extensor hallucis brevis muscle and the adductor hallucis muscle of the affected foot. In some embodiments, the neuromuscular toxin is injected into the flexor hallucis brevis muscle and the adductor hallucis muscle of the affected foot. In some embodiments, the neuromuscular toxin is injected into the extensor hallucis brevis muscle, the flexor hallucis brevis muscle, and the adductor hallucis muscle of the affected foot. In some embodiments, injection in the adductor hallucis muscle comprises injection into the oblique head and/or transverse heads of the adductor hallucis muscle. In some embodiments, injection in the oblique head of the adductor hallucis muscle comprises injection in one or more of the medial, central and lateral components. In some embodiments, injection in the transverse head of the adductor hallucis muscle comprises injection in one or more of the medial, central and lateral components. In some embodiments, injection in the flexor hallucis brevis muscle comprises injection into the lateral head and/or medial heads of the flexor hallucis brevis muscle. In some embodiments, said muscles are injected with the neuromuscular toxin simultaneously. In some embodiments, said muscles are injected with the neuromuscular toxin sequentially (e.g, on separate days and/or separate procedures). In some embodiments, the same muscle of the affected foot is injected with a neuromuscular toxin on multiple occasions (e.g, on separate days and/or separate procedures). In some embodiments, a different muscle of the affected foot is injected with a neuromuscular toxin during a subsequent treatment.

In some embodiments, electromyography and/or electrical stimulation employed to determine the optimal sites within the one or muscles for injection of the neuromuscular toxin. In some embodiments, the neuromuscular toxin is injected under ultrasound guided electrical stimulation. In some embodiments, an INOJECT needle electrode is employed to guide injection. In some such embodiments, the placement of the lead (e.g, gel electrode) is the patient's thigh. In some embodiments, enhanced contrast for ultrasonic guided injections is obtained by introducing gas bubbles combined with the toxin. In some embodiments, muscle receptor binding is visualized by combining a ligand for muscle (e.g., G protein coupled ligand receptors, muconotoxin GIIIA) with the toxin. In still further embodiments, ligands associated with inflammation (e.g., the selectin family of carbohydrate binding proteins, inducible T-cell co-stimulator ligand (ICOSLG)) is employed to enhance visualization under ultrasound for inflamed muscle. In some embodiments, determination of injection site is performed using a DIGISTIM III peripheral nerve/muscle stimulator. In some embodiments, the oblique head of the adductor hallucis muscle is stimulated moving distal to proximal. In some embodiments, the transverse head of the adductor hallucis muscle is stimulated moving medial to lateral. In some embodiments, a dynometer is attached to the hallux to quantify the strength of the stimulus at each level (e.g. by measuring adduction of the hallux towards the second toe) and the toxin is delivered only to the areas deemed most effective. In some embodiments, a 27-gauge needle in a 3-cc tuberculin syringe is employed to deliver the toxin directly into the muscle. In some embodiments, a longer needle (e.g., 2-3 cm) is employed. In some embodiments, injection is performed approaching from the plantar aspect of the foot. In some such embodiments, a posterior tibial nerve block is applied prior to introduction of the needle using an anesthetic (e.g., lidocaine or bupivacaine). In some embodiments, the neuromuscular toxin is administered during surgery on the foot. In some embodiments, the foot surgeries comprise simple bunion removal, distal first metatarsal osteotomies, proximal first metatarsal osteotomies, metatarsal-cuneiform joint procedures, and hallux osteotomies. In some embodiments, the osteotomy is an Austin osteotomy, Modified Austin osteotomy, Reverdin osteotomy with modifications, Scarf osteotomy, Mitchell osteotomy, or Hohman osteotomy.

Botulinum Toxins

As used herein, the term "neuromuscular toxin" (abbreviated as "toxin") refers to a compound capable of interfering with the connection between muscle and nerve. In some embodiments, the toxin is an inhibitor of acetylcholine release. In some embodiments, the toxin is a botulinum toxin (BT). In some embodiments, the BT is one or more of *Clostridium botulinum* type A neurotoxin, BTTA; *Clostridium botulinum* type B neurotoxin, BTTB; *Clostridium botulinum* type C1 neurotoxin, BTTC1; *Clostridium botulinum* type C2 neurotoxin, BTTC2; *Clostridium botulinum* type C3 neurotoxin, BTTC3; *Clostridium botulinum* type D neurotoxin, BTTD; *Clostridium botulinum* type E neurotoxin, BTTE; *Clostridium botulinum* type F neurotoxin, BTTF; and/or *Clostridium botulinum* type G neurotoxin polypeptide, BTTG. In some embodiments, the toxin is one or more of MYOBLOC: (Solstice), DYSPORT: (Ipsen), XEOMIN: (Merz), RToo2: (Revance Therapeutics), Nabota (Daewoong), Botulox (Hugel), Innotox (Medytox) Neuronox (Medytox), Siax (Medytox), Meditoxin (Medytox), and/or Koreatox (Medytox). In some embodiments, the toxin one or more of tetanus toxins, tetrodotoxin, difficile toxins, butyricum toxins, staphylococcal alpha-toxin and/or animal venoms known in the art. Non-limiting examples of toxins further include recombinant, synthetic, and derivatives of neuromuscular toxins. In some embodiments, the toxin is synthetically produced using in vitro protein synthesizing techniques.

In some embodiments, toxin derivatives include fragments, subunits, and chimeras of neuromuscular toxins. In some embodiments, the toxin is a polypeptide having at least 80% amino acid identity, preferably 85%, 90%, 95%, or higher, up to and including 100% identity, with active toxin, and which exhibits a neurotoxic activity e.g. it blocks neurotransmitter release at peripheral cholinergic nerve terminals such as the neuromuscular junction. In some embodiments, the toxin is a functional fragment of an active toxin and which exhibits a neurotoxic activity e.g. a portion of BT which blocks neurotransmitter release at peripheral cholinergic nerve terminals such as the neuromuscular junction. A functional fragment of an active toxin polypeptide may comprise at least 10, 20, 30, 40, 50, 60, 70, 80, 90, or 95% of the amino acids of the sequence represented by the native sequence.

In some embodiments, a combination of two or neuromuscular toxins are administered to the affected foot. In some embodiments, the combination of neuromuscular toxins are administered simultaneously. In some embodiments, the combination of neuromuscular toxins are administered sequentially (e.g, on separate days and/or separate procedures). In some embodiments, the combination of toxins causes longer-lasting action than with a single toxin. In some embodiments, same neuromuscular toxin is administered in multiple procedures to the same affected foot. In some embodiments, a different neuromuscular toxin is administered during a subsequent treatment.

The dose of toxin administered to the affected foot will depend upon the severity of the condition (e.g. the size of the area requiring treatment, the age and size of the patient and the potency of the toxin). In some embodiments, the dose of the neuromuscular toxin administered to the affected foot is from about 1 to about 1000 units. For example, a single dose can have about, less than about, or more than about 5 units, 10 units, 15 units, 20 units, 15 units, 30 units, 35 units, 40 units, 45 units, 50 units, 55 units, 60 units, 70 units, 80 units, 90 units, 100 units, 120 units, 140 units, 160 units, 180 units, 200 units, 225 units, 250 units, 275 units, 300 units, 350 units, 400 units, 450 units, 500 units, 600 units, 700 units, 800 units, 900 units, or 1000 units of toxin. In one embodiment, the dosage for BT type A is from about 50 units to about 300 units. In some embodiments, the range of dosage of BT type A is from about 75 units to about 100 units. In some embodiments, the dose of BT is $10^{-3}$ to 35 U/kg, $10_{-2}$ to 25 U/kg, $10_{-2}$ to 15 U/kg, 1 to 10 U/kg, $10^{-3}$ to 2000 U/Kg, 1 to 40000 U/Kg, $10_{-2}$ to 200 U/kg, $10^{-1}$ to 35 U/kg, $10^{-3}$ to 2000 U/Kg, 0.5 to 500 U/Kg, 0.5 to 1000 U/Kg, 0.5 to 2000 U/Kg, 0.5 to 3000 U/Kg, 10 to 500 U/Kg, 10 to 1000 U/Kg, 10 to 2000 U/Kg, or 10 to 3000 U/Kg. In some embodiments, said doses comprise the sum total of the neuromuscular toxin administered to an affected foot during a single treatment. In some embodiments, said doses comprise the amount neuromuscular toxin administered to a single muscle during a single procedure. In some embodiments, the methods disclosed herein provide the advantage or requiring less toxin to be administered to the patient to achieve comparable results.

Reference to "units" herein is with respect to units of BOTOX (Allergan) unless specifically noted otherwise. The following is a list of commercially-available botulinum toxins with an approximate dosage equivalency ratio relative to BOTOX. That is, the approximate dosage equivalency ratio is provided because the potency of botulinum toxins may vary between manufacturers. Therefore, an approximate dosage equivalency ratio relative to BOTOX, which was used in the above-described treatments, is provided for each of the following commercially-available botulinum toxins.

1. DYSPORT: (Ipsen): Ranges from 2.5-3.0:1 ratio to Botox.
2. XEOMIN: (Merz): 1:1 equivalent to Botox
3. RToo2: (Revance Therapeutics): 2:1 ratio to Botox
4. Nabota: (Daewoong): 1:1 Botox
5. Botulox: (Hugel): 1:1 Botox
6. Innotox: (Medytox): 1:1 Botox
7. Neuronox, Siax, Meditoxin, Koreatox: (Medytox): 1:1 Botox
8. MYOBLOC: (Solstice): In the treatment of dystonia 400-10,000 MYOBLOC-units are generally employed. However, no established ratios of MYOBLOC-units to units of Botox are defined. The specific dosage for treatments described in the present application can be established through routine pharmacological testing.

In some embodiments, a comparison of pre- and post-procedural measurements of the intermetatarsal angle, the hallux abductus angle, and/or the tibial sesamoid position is used to determine whether further treatment is required. In some embodiments, multiple administrations of the neuromuscular toxin to one or more muscles of the affected foot are performed. In some embodiments, the procedures are performed at intervals of about 1 to 2 weeks, about 2 to 3 weeks, about 3 to 4 weeks, about 4 to 5 weeks, about 5 to 6 weeks, about 6 to 7 weeks, about 7 to 8 weeks, about 7 to 8 weeks, about 8 to 10 weeks, about 10 to 12 weeks, about 3 to 6 months, about 6 to 9 months, or about 9 to 12 months.

In some embodiments, the methods disclosed herein, either as single injection of a toxin into a muscle of the affected foot, or as combination administration of the toxin to a plurality of muscles of the affected foot, are effective for treating abnormalities of the first metatarsophalangeal joint of the foot, as measured by a decrease in the intermetatarsal angle between the line of the first and second metatarsal, a decrease in the hallux abductus angle, and/or a decrease in the tibial sesamoid position. The methods provided herein can have a measured effect that is an improvement of about, or greater than about, 5, 10, 15, 20, 30, 50, 75, 100, 110, 120, 150, 200, 250, 350, 500, 700, or 1000% over a control subject or control group.

In some embodiments, methods disclosed herein can decrease the intermetatarsal angle between the line of the first and second metatarsal. In some embodiments, the rate of decrease of the intermetatarsal angle is increased in a patient receiving or received treatment by at least, or at least about, 5%, 10%, 20%, 30%, 40%, 50%, 60%, 70%, 80%, or 90% as compared to the patients received no treatment. In some embodiments, the methods herein cause a decrease in the intermetatarsal angle between the line of the first and second metatarsal by about, 5%, 10%, 20%, 30%, 40%, 50%, 60%, 70%, 80%, 90%, or a range between any two of these values as compared to the patients received no treatment.

In some embodiments, methods disclosed herein can decrease the hallux abductus angle. In some embodiments, the rate of decrease of the hallux abductus angle is increased in a patient receiving or received treatment by at least, or at least about, 5%, 10%, 20%, 30%, 40%, 50%, 60%, 70%, 80%, or 90% as compared to the patients received no treatment. In some embodiments, the methods herein cause a decrease in the hallux abductus angle by about, 5%, 10%, 20%, 30%, 40%, 50%, 60%, 70%, 80%, 90%, or a range between any two of these values as compared to the patients received no treatment.

In some embodiments, methods disclosed herein can decrease the tibial sesamoid position. In some embodiments, the rate of decrease of the tibial sesamoid position is increased in a patient receiving or received treatment by at least, or at least about, 5%, 10%, 20%, 30%, 40%, 50%, 60%, 70%, 80%, or 90% as compared to the patients received no treatment. In some embodiments, the methods herein cause a decrease in the tibial sesamoid position by about, 5%, 10%, 20%, 30%, 40%, 50%, 60%, 70%, 80%, 90%, or a range between any two of these values as compared to the patients received no treatment.

Additional non-limiting examples of such advantages of the methods disclosed herein include, but are not limited to, reduced foot pain, reduced side effects, increased range of motion of the joint, a reduction in the amount of toxin required to be administered, and/or reduced recuperation time, quicker return of the patient to ambulatory status. In some embodiments, the pain associated with abnormalities of the first metatarsophalangeal joint can be successfully treated regardless of whether structural changes in the underlying abnormality occur.

As discussed in further detail below, it has been unexpectedly discovered that intramuscular injection of toxin into the extensor hallucis brevis muscle alone can significantly reduce symptoms of a variety of the abnormalities of the foot referred to herein, including hallux abductovalgus. Surprisingly, combination treatment with intramuscular toxin into other muscles of the foot, including the adductor hallucis more commonly associated with hallux abductovalgus, as well as in combination with intramuscular injection into the flexor hallucis brevis muscle of the affected foot, can result in unexpected synergistic effects. Thus, as disclosed herein, administration of neuromuscular toxins to two or more muscles of the affected foot can result in synergistic effects in treating abnormalities of the first metatarsophalangeal joint of the foot. These synergistic effects can be such that the one or more effects of the combination administration are greater than the one or more effects of each administration alone at a comparable dosing level, or they can be greater than the predicted sum of the effects of all of the administrations at a comparable dosing level, assuming that each administration acts independently. The synergistic effect can be about, or greater than about, 5, 10, 20, 30, 50, 75, 100, 110, 120, 150, 200, 250, 350, or 500% better than the effect of treating a subject with one of the components alone, or the additive effects of each of the muscles when administered alone. The effect can be any of the measurable effects described herein. The method comprising injection of a plurality of muscles of the affected foot can be such that the synergistic effect can be measured as a reduction in intermetatarsal angle and that intermetatarsal angle is decreased to a greater degree as compared to the sum of the effects of injecting each single muscle, determined as if each injected muscle exerted its effect independently, also referred to as the predicted additive effect herein. For example, if a method comprising injection of muscle (a) yields an effect of a 20% improvement in intermetatarsal angle and a method comprising injection of muscle (b) yields an effect of 50% improvement in intermetatarsal angle, then a method comprising injection of both muscle (a) and muscle (b) would have a synergistic effect if the combination of injections had effect on intermetatarsal angle greater than 70%.

A synergistic combination co-administration to a plurality of muscles of the affected foot can have an effect that is greater than the predicted additive effect of each administration alone as if each administration exerted its effect independently. For example, if the predicted additive effect is 70%, an actual effect of 140% is 70% greater than the predicted additive effect or is 1 fold greater than the predicted additive effect. The synergistic effect can be at least about 20, 50, 75, 90, 100, 150, 200 or 300% greater than the predicted additive effect. In some embodiments, the synergistic effect can be at least about 0.2, 0.5, 0.9, 1.1, 1.5, 1.7, 2, or 3 fold greater than the predicted additive effect.

In some embodiments, the synergistic effect of the toxin administration to two or more muscles of the affected foot can also allow for reduced dosing amounts, leading to reduced side effects to the subject and reduced cost of treatment. Furthermore, the synergistic effect can allow for results that are not achievable through any other treatments. Therefore, proper identification of multiple muscles of the affected foot suitable for injection can allow for significant improvements in the treatment of abnormalities of the first metatarsophalangeal joint.

The methods described herein may be combined with other modalities to achieve additive or synergistic effects. These other modalities include, but are not limited to: use of a dynometer on the hallux to quantify the strength of the stimulus at each level; immobilizing the foot after the toxin has been administered with a splint, surgical shoe, ridged sole shoe, casting, gauze, and/or tape; selective injection into specific fascicles; and/or aspirating so as to avoid injection of the toxin into the artery of a first inner-space of the artery.

EXAMPLES

Exemplary embodiments disclosed in U.S. Pat. No. 7,276,244 include the following Examples 1 and 2 will now be illustrated by reference to the following nonlimiting examples.

In each example, appropriate areas were injected with a sterile solution containing Botulinum toxin (e.g. 100 units BOTOX solubilized in 0.9% sterile saline without preservative). Determination of the site to inject was performed using a DIGISTIM III peripheral nerve/muscle stimulator and an INOJECT needle electrode, with placement of the lead (gel electrode) in the patient's thigh.

Example 1

A female patient suffering from hallux abductovalgus was treated with 100 units of botulinum toxin type A by direct injection of the toxin into the adductor hallucis muscle. Determination of the injection sites was performed by placing the INOJECT needle from the dorsal mid first interspace of the foot proximal to the first and second metatarsophalangeal joint and delivering a 2 Hz pulse while advancing the needle in the direction of the transverse adductor hallucis muscle belly. Once a motor response was elicited (pulsating abduction of the hallux), 25 units of the toxin were injected into the transverse belly of the adductor hallucis muscle. The needle was then partially retracted and redirected upward toward the oblique arm of the adductor hallucis muscle and advanced plantarly until a motor response was elicited (adduction of the hallux). At this point, 75 units of the toxin were injected into the oblique adductor hallucis muscle. Within 1 week, the symptoms of hallux abductovalgus were markedly reduced.

The patient was followed for 41 days following injection, with pre and post procedure measurements of radiographs obtained to monitor the patient's progress. Before the procedure, the patient exhibited an intermetatarsal angle of 14 degrees, a tibial sesamoid position of 4, and a hallux abductus angle of 20 degrees. Twenty four days following injection, the patient's intermetarsal angle was reduced to 10 degrees, her tibial sesamoid position was 3, and her hallux abductus angle was 10 degrees. Forty one days following injection, the patient's intermetarsal angle was further reduced to 9 degrees, her tibial sesamoid position was 2, and her hallux abductus angle was 7 degrees. Through day 41, the patient has reported none of her previous symptoms associated with hallux abductovalgus.

Example 2

A female patient suffering from hallux limitus was treated with 100 units of botulinum toxin type A by direct injection of the toxin into the Flexor Hallucis Brevis (FHB) muscle. Determination of the injection sites was performed by placing the INOJECT needle through the skin from the dorsum of the foot at the mid first interspace proximally and applying stimulation while advancing the needle in a plantar medial direction to the lateral belly of the Flexor Hallucis Brevis. Once location was confirmed with a motor response of plantar flexion of the first metatarsophalangeal joint, 50 units of toxin were injected into the lateral belly of the Flexor Hallucis Brevis muscle. The medial belly of the Flexor Hallucis Brevis muscle was then approached with the needle through the medial aspect of the foot where the muscle can be palpated. The needle was advanced transversely from about the level of the first metatarsal until a motor response of plantar flexion of the first metatarsophalangeal joint was elicited. At this point, 50 units of toxin were injected into the medial belly of the Flexor Hallucis Brevis muscle.

Within 3 days, the symptoms of hallux limitus were markedly reduced. Before treatment, the patient exhibited a range of motion at the first metatarsophalangeal joint of 30 degrees with pain upon range of motion. One week after injection, the patient exhibited a range of motion of 50 degrees at the first metatarsophalangeal joint with no pain at the end range of motion. At week 6, the patient exhibited a range of motion of 55 degrees at the first metatarsophalangeal joint with no pain upon range or end range of motion.

The inventor has discovered that surprising improvements in the results obtained using embodiments of the invention disclosed in U.S. Pat. No. 7,276,244 can be obtained by employing certain additional techniques. For example, ultrasound can be employed to guide the site of injection of toxin. This can be useful in placing the toxin into the appropriate anatomical structures while avoiding major components of the vasculature, which can result in severe complications including death.

There are at least four areas that can be distinguished under ultrasound that can be involved in providing effective treatment. There are three individual fascicles/components of the oblique head of the adductor hallucеs, the medial, central and lateral components. In addition, the transverse head has a component that can be a site for treatment. There are also 3 fascicles of the transverse head. Although these are quite small and often difficult to distinguish under ultrasound, the use of enhanced ultrasound and robotic techniques can be employed to precisely deliver toxin to involved fascicles.

The three areas of the oblique head can be stimulated moving distal to proximal and the area of the transverse head can be stimulated moving medial to lateral. Each of the areas can be individually injected under ultrasound guided electrical stimulation. Surprisingly, through the use of such guidance, reduction in the amount of toxin required and decrease in untoward side effects can be achieved.

Enhanced contrast for ultrasonic guided injections can be obtained by introducing gas bubbles combined with the toxin. Additionally, muscle receptor binding can be visualized by combining a ligand for muscle with the toxin. A number of such ligands are known to those skilled in the art. For example, G protein coupled ligand receptors are present in striated muscle and ligands for such receptors can be employed. Another ligand associated with muscle is mu-conotoxin GIIIA, which is a peptide ligand for muscle sodium channels. Ligands associated with inflammation can also be employed to enhance visualization under ultrasound for inflamed muscle. Such ligands can include one or more of the selectin family of carbohydrate binding proteins and inducible T-cell co-stimulator ligand (ICOSLG). These ligands are present in inflammation and can be used as to identify sites of inflammation in combination with injection of toxin.

In addition, prior to injection, each of the areas can be stimulated systematically to ascertain the most effective areas of end plate clusters for that fascicle. In this regard, a dynometer can be attached to the hallux to quantify the strength of the stimulus at each level, e.g. by measuring adduction of the hallux towards the second toe. Toxin can be delivered only to the areas deemed most effective or the dosage to each area can be adjusted depending on the response to stimulation.

It has also been discovered that injecting the Extensor Hallucis Brevis muscle either alone or in combination with other sites can provide more effective relief. In many cases this muscle is a contributing adductor of the hallux, relative to the second metatarsal.

Unexpected improvements in results can also be obtained by aspirating so as to avoid injection or spread of the toxin into the artery of the first inner-space. Avoiding this space will avoid many complications associated with injection of toxin.

Yet another unexpected improvement can be obtained by application of a bunion splint and/or an abductor hallucis muscle stimulator, such as that developed by Dr. Bassem Demian and sold by Geninar, Inc. under the trademark Bunionase™. Advantageously, the patient receiving toxin treatment can self-apply these ancillary treatments at times convenient for the patient, especially at night.

Additional unexpected improvements can be obtained by using a longer needle, e.g. 2-3 cm and approaching from the plantar aspect of the foot. When using a larger needle, Posterior Tibial nerve block can be applied prior to introduction of the needle using an anesthetic such as Lidocaine or Bupivicaine.

While particular forms and embodiments have been described, it will be apparent that these and other embodiments can also be embodied in other specific forms without departing from the spirit and scope thereof.

Example 3

A radiographic comparison study of the Hallux Abductus (HA) angles, 1st Intermetatarsal (IM) Angles and Tibial Sesamoid Positions (TSP) was done on the same patient PR with almost identical bilateral HAV deformities to assess the contribution to reduction of the HAV deformity with the Extensor Hallucis Brevis (EHB) injection (INJECTION B) as an isolated procedure and as an improvement/adjunct to the original isolated procedure (INJECTION A).

Figure 2:
FIG. 2 is a radiograph of the left and right feet of the patient in Example 3 illustrating reduction of actual valgus rotation of the big toes at 21 days post-injection of INJECTION A in the left foot and INJECTION B in the right foot.
Figure 3:
FIG. 3 is a radiograph of the left and right feet of the patient in Example 3 illustrating reduction of actual valgus rotation of the big toes at 42 days post-injection of INJECTION A and 21 days post-injection of INJECTION B in the left foot and 42 days post-injection of INJECTION B and 21 days post-injection of INJECTION A in the right foot.

FIGS. 1-3 are radiographs of right and left feet of the patient taken at pre-injection, 21 days post-injection and 42 days post-injection, respectively. All radiographs were positioned and taken by the same technician with the patient in their natural weight bearing angle and base of gait. Comparisons for this study were AP views at 13 degrees from vertical taken prior to treatment and then at 3 week intervals×2 after each injection.

The first injection series was as follows (immediately after initial radiographs):
Right foot, 25 units Botulinum toxin A to the Extensor Hallucis Brevis (EHB) [INJECTION B]
Left foot, 75 units to the oblique, 25 units to transverse heads of the Adductor Hallucis (AdH) [INJECTION A]
The second injection series was as follows (immediately after 3 week post initial injection radiographs):
Right foot, 75 units to the oblique, 25 units to transverse heads of the AdH [INJECTION A]
Left foot, 25 units Botulinum toxin A to the EHB [INJECTION B]

TABLE 1

| | Left Foot | | |
| | Initial | INJ. A | INJ. B |
|---|---|---|---|
| IM | 14 | 10 | 9 |
| HA | 20 | 10 | 5 |
| TSP | 4 | 3 | 2 |

TABLE 2

| | Right Foot | | |
| | Initial | INTJ. A | INTJ. B |
|---|---|---|---|
| IM | 13 | 11 | 9 |
| HA | 20 | 12 | 5 |
| TSP | 3 | 2 | 2 |

As shown in Table 1 and when comparing FIGS. 1 and 2, following the injecting of INJECTION A into the oblique and transverse heads of the Adductor Hallucis (AdH) of the left foot, the patient exhibited a reduction in intermetatarsal angle, hallux abductus angle and tibial sesamoid position. As shown in FIG. 1, which is a radiograph of the left foot taken before the procedure, the patient's left foot exhibited an intermetatarsal angle of 14 degrees, a hallux abductus angle of 20 degrees and a tibial sesamoid position of 4. As shown in FIG. 2, which is a radiograph taken at twenty one days following the injecting of INJECTION A into the patient's left foot, the patient's intermetarsal angle was reduced to 10 degrees, her hallux abductus angle was 10 degrees and her tibial sesamoid position was 3.

The patient's left foot was then injected with INJECTION B into the extensor hallucis brevis muscle after the injecting of INJECTION A into the oblique and transverse heads of the adductor halluces. Following the injecting of INJECTION B into the extensor hallucis brevis muscle, the patient exhibited an unexpected further reduction in intermetatarsal angle, hallux abductus angle and tibial sesamoid position of the left foot when compared to the injecting of INJECTION A alone. As shown in Table 1 and illustrated in FIG. 3, which is a radiograph of the left foot taken at forty two days following injection of INJECTION A and twenty one days following injection of INJECTION B, the patient's intermetarsal angle was further reduced to 9 degrees, her hallux abductus angle was 5 degrees and her tibial sesamoid position was 2. That is, following the injecting of INJECTION B in addition to INJECTION A into the patient's left foot, the patient exhibited further reduction in valgus rotation of the big toe than when compared to the injecting of INJECTION A alone.

The injecting of INJECTION B into the extensor halluces brevis alone also provided an unexpected reduction in intermetatarsal angle, hallux abductus angle and tibial sesamoid position of the big toe. As shown in Table 2 and illustrated in FIG. 1, which is a radiograph of the right foot before the procedure, the patient's right foot exhibited an intermetatarsal angle of 13 degrees, a hallux abductus angle of 20 degrees and a tibial sesamoid position of 3. When compared with FIG. 2, which is a radiograph of the right foot taken at twenty one days following injection of INJECTION B into the extensor halluces brevis of the patient's right foot, the patient's intermetarsal angle in the right foot was reduced to 11 degrees, her hallux abductus angle was 12 degrees and her tibial sesamoid position was 2. That is, following the injecting of INJECTION B into the extensor halluces brevis alone into the patient's right foot, the patient exhibited further reduction in valgus rotation of the big toe.

The patient's right foot was then injected with INJECTION A into the oblique and transverse heads of the adductor halluces after the injecting of INJECTION B into the extensor hallucis brevis. Following the injecting of INJECTION A into the oblique and transverse heads of the adductor halluces, the patient exhibited an unexpected further reduction in intermetatarsal angle, hallux abductus angle and tibial sesamoid position of the left foot when compared to the injecting of INJECTION B alone. As shown in Table 2 and illustrated in FIG. 3, which illustrates the right foot at forty two days following injection of INJECTION B into the patient's right foot and twenty one days following injection of INJECTION A into the patient's right foot, the patient's intermetarsal angle was further reduced to 9 degrees, her hallux abductus angle was reduced to 5 degrees and her tibial sesamoid position decreased to 2. That is, following the injecting of INJECTION A after the injecting of INJECTION B, the patient exhibited further reduction in valgus rotation of the big toe than when compared to the injecting of INJECTION B alone.

The above data in Tables 1 and 2 and FIGS. 1-3 show that INJECTION B is an improvement to the application of INJECTION A in the reduction of the two main radiographic measurement angles and as well as TSP in evaluating severity of the hallux abducto valgus deformity. Of note is that at 6 weeks, both bunions were pain free and there was a reduction of the actual valgus rotation of the big toes (paralleling of the big toe nail to the transverse surface plane).

Example 4

A radiographic comparison study of the Hallux Abductus (HA) angles, 1st Intermetatarsal (IM) Angles and Tibial Sesamoid Positions (TSP) was done on the same patient AL with almost identical bilateral HAV deformities to assess the contribution to reduction of the HAV deformity with the EHB injection (INJECTION B and INJECTION C) in combination with (INJECTION A) to the left foot as an improvement/adjunct to the original isolated procedure (INJECTION A) to the right foot.

FIGS. 4-7 are radiographs of the right foot of the patient taken at pre-injection, 27 days post-injection, 43 days post-injection and 63 days post-injection, respectively. FIGS. 8-11 are radiographs of the left foot of the patient taken at pre-injection, 21 days post-injection, 35 days post-injection and 63 days post-injection, respectively. All radiographs were positioned and taken by the same technician with the patient in their natural weight bearing angle and base of gait. Comparisons for this study were AP views at 13 degrees from vertical taken prior to treatment and then at 2-4 week intervals×3 after each injection.

The injections were as follows (immediately after initial radiographs):
  Left foot, 25 units Botulinum toxin A to the Extensor Halluces Brevis (EHB) [INJECTION B], 25 units to the lateral head of Flexor Halluces Brevis (FHB) [INJECTION C], and 75 units to the oblique, 25 units to transverse heads of the Adductor Hallucis (AdH) [INJECTION A],
  Right foot, 75 units to the oblique, 25 units to transverse heads of the AdH [INJECTION A]

TABLE 3

| | Right Foot (INJ. A) | | | |
| --- | --- | --- | --- | --- |
| | Initial | 4 wks | 6 wks | 9 wks |
| IM | 12 | 10 | 10 | 10.1 |
| HA | 20 | 16 | 15 | 15 |
| TSP | 6 | 4 | 4 | 4 |

TABLE 4

| | Left Foot (INJ. A/B/C) | | | |
| --- | --- | --- | --- | --- |
| | Initial | 3 wks | 5 wks | 9 wks |
| IM | 12 | 7 | 7 | 7 |
| HA | 20 | 15 | 10 | 10 |
| TSP | 6 | 5 | 4+ | 4 |

When comparing the reduction of the valgus rotation of the big toe following the injecting of INJECTION A into the oblique and transverse heads of the adductor hallucis, INJECTION B into the extensor halluces brevis, and INJECTION C into the lateral head of the flexor halluces brevis, the patient exhibited an unexpected reduction in intermetatarsal angle, hallux abductus angle and tibial sesamoid position when compared to the injecting of INJECTION A into the oblique and transverse heads of the adductor halluces alone.

Figure 4:
FIG. 4 is a radiograph of the right foot of the patient receiving the treatment described in Example 4. The radiograph illustrates the right foot prior to injection of INJECTION A.
Figure 5:
FIG. 5 is a radiograph of the right foot of the patient in Example 4. The radiograph illustrates reduction of actual valgus rotation of the big toe at 27 days post-injection of INJECTION A.
Figure 6:
FIG. 6 is a radiograph of the right foot of the patient in Example 4. The radiograph illustrates reduction of actual valgus rotation of the big toe at 43 days post-injection of INJECTION A
Figure 7:
FIG. 7 is a radiograph of the right foot of the patient in Example 4. The radiograph illustrates reduction of actual valgus rotation of the big toe at 63 days post-injection of INJECTION A.

As shown in Table 3 and as illustrated in FIG. 4, which is a radiograph of the patient's right foot taken prior to the injecting of INJECTION A, the patient's initial intermetarsal angle was 12 degrees, her hallux abductus angle was 20 degrees and her tibial sesamoid position was 6. After 4 weeks following the injecting of INJECTION A, the patient exhibited an initial reduction in valgus rotation. As shown in FIG. 5, the patient's right foot exhibited an intermetarsal angle of 10 degrees, a hallux abductus angle of 16 degrees and a tibial sesamoid position of 4. After 6 weeks following the injecting of INJECTION A, the patient exhibited further but slight reduction in valgus rotation. As shown in Table 3 and as illustrated in FIG. 6, the patient's right foot exhibited an intermetarsal angle of 10 degrees, a hallux abductus angle of 15 degrees and a tibial sesamoid position of 4. After 9 weeks following the injecting of INJECTION A, the patient exhibited little to no further reduction in valgus rotation. As shown in Table 3 and as illustrated in FIG. 7, the patient's right foot exhibited an intermetarsal angle of 10.1 degrees, a hallux abductus angle of 15 degrees and a tibial sesamoid position of 4. In total, the patient exhibited an intermetarsal angle reduction of approximately 2 degrees, a hallux abductus angle reduction of 5 degrees and a reduction of tibial sesamoid position of 2.

In contrast, the patient exhibited greater valgus rotation reduction of the big toe following the injecting of INJECTION A into the oblique and transverse heads of the adductor hallucis, INJECTION B into the extensor halluces brevis, and INJECTION C into the lateral head of the flexor halluces brevis.

Figure 8:
FIG. 8 is a radiograph of the left foot of the patient receiving the treatment described in Example 4. The radiograph illustrates the left foot prior to injection of INJECTION A, INJECTION B and INJECTION C.

As shown in Table 4 and as illustrated in FIG. 8, which is a radiograph of the patient's right foot taken prior to the injecting of INJECTIONS A/B/C, the patient's initial intermetarsal angle was 12 degrees, her hallux abductus angle was 20 degrees and her tibial sesamoid position was 6. After 3 weeks following the injecting of INJECTIONS A/B/C, the patient exhibited an initial reduction in valgus rotation that was greater than the initial reduction in valgus rotation of just INJECTION A alone.

Figure 9:
FIG. 9 is a radiograph of the left foot of the patient in Example 4. The radiograph illustrates reduction of actual valgus rotation of the big toe at 21 days post-injection of INJECTION A, INJECTION B and INJECTION C.

As shown in Table 4 and as illustrated in FIG. 9, the patient's right foot exhibited an intermetarsal angle of 7 degrees, a hallux abductus angle of 15 degrees and a tibial sesamoid position of 5. When compared to the valgus rotation reduction at 4 weeks following the injecting of just INJECTION A alone, the injecting of INJECTIONS A/B/C provided an additional reduction of intermetarsal angle of 3 degrees and hallux abductus angle of 1 degrees. After 5 weeks following the injecting of INJECTIONS A/B/C, the patient exhibited further reduction in valgus rotation when compared to the results after 3 weeks.

Figure 10:
FIG. 10 is a radiograph of the left foot of the patient in Example 4. The radiograph illustrates reduction of actual valgus rotation of the big toe at 35 days post-injection of INJECTION A, INJECTION B and INJECTION C.

As shown in Table 4 and as illustrated in FIG. 10, the patient's right foot exhibited an intermetarsal angle of 7 degrees, a hallux abductus angle of 10 degrees and a tibial sesamoid position of 4+. When compared to the valgus rotation reduction at 6 weeks following the injecting of just INJECTION A alone, the injecting of INJECTIONS A/B/C provided an additional reduction of intermetarsal angle of 3 degrees and hallux abductus angle of 5 degrees. After 9 weeks following the injecting of INJECTIONS A/B/C, the patient exhibited slight reduction in valgus rotation when compared to the results after 5 weeks.

Figure 11:
FIG. 11 is a radiograph of the left foot of the patient in Example 4. The radiograph illustrates reduction of actual valgus rotation of the big toe at 63 days post-injection of INJECTION A, INJECTION B and INJECTION C.

As shown in Table 4 and as illustrated in FIG. 11, the patient's right foot exhibited an intermetarsal angle of 7 degrees, a hallux abductus angle of 10 degrees and a tibial sesamoid position of 4. When compared to the valgus rotation reduction at 9 weeks following the injecting of just INJECTION A alone, the injecting of INJECTIONS A/B/C provided a further reduction of intermetarsal angle of 3.1 degrees and hallux abductus angle of 5 degrees.

The above data and figures show that INJECTION B and INJECTION C are an initial and sustainable improvement to the application of INJECTION A in the reduction of the two main radiographic measurement angles (IM and HA) when compared to INJECTION A alone. Further, in some embodiments, injecting the lateral head of Flexor Halluces Brevis is an improvement to the injection paradigm for treatment of hallux valgus. In other embodiments, injecting the lateral head of FHB and not injecting the medial head of FHB is an improvement to the injection paradigm for treatment of hallux valgus.

What is claimed is:

1. A method for treating an abnormality of the first metatarsophalangeal joint of the foot of a mammal comprising:

electrically stimulating the extensor hallucis brevis muscle of a foot of the mammal affected by the abnormality;

visually confirming that the stimulated extensor hallucis brevis muscle responds to the stimulating by contracting, electrically stimulating the oblique head of the adductor hallucis muscle of the foot of the mammal moving distal to proximal and electrically stimulating the transverse head of the adductor hallucis muscle of the foot of the mammal moving medial to lateral;

visually identifying the sites on the stimulated adductor hallucis muscle that respond most strongly to the stimulating; and administering an amount of botulinum toxin effective to treat said abnormality via muscular injection to the extensor hallucis brevis muscle and to the sites on the adductor hallucis muscle of the affected foot that respond most strongly to the stimulating.

2. The method of claim 1, wherein a dynometer is attached to the hallux to quantify the strength of the stimulus at each level.

3. The method of claim 2, wherein the strength is measured by measuring adduction of the hallux towards the second toe.

4. The method of claim 1, wherein the stimulating is conducted using a DIGISTIM III peripheral nerve/muscle stimulator.

5. The method of claim 1, wherein both the stimulating and the administering are conducted using a needle configured to both stimulate and administer.

6. The method of claim 1, further comprising electrically stimulating the flexor hallucis brevis muscle of a foot of the mammal affected by the abnormality and visually confirming that the stimulated flexor hallucis brevis muscle responds to the stimulating by contracting.

7. The method of claim 6, wherein the needle is placed through the skin from the dorsum of the foot at the mid first interspace proximally and applying stimulation while advancing the needle in a plantar medial direction to the lateral belly of the flexor hallucis brevis muscle.

8. The method of claim 1, wherein the each of the stimulating steps comprises attaching an injectable needle to an electrode; inserting the injectable needle through the skin and into the target muscle; applying electrical stimulation as the needle as the needle is advanced into the muscle to deliver an electrical stimulation and elicit a motor response.

* * * * *

UNITED STATES PATENT AND TRADEMARK OFFICE
CERTIFICATE OF CORRECTION

PATENT NO. : 10,869,914 B2
APPLICATION NO. : 16/734251
DATED : December 22, 2020
INVENTOR(S) : Philip Andrew Radovic It is certified that error appears in the above-identified patent and that said Letters Patent is hereby corrected as shown below:

In the Specification

In Column 2, Line 40, delete "injection" and insert --injection.--.

In Column 2, Line 60, delete "dynometer" and insert --dynamometer--.

In Column 3, Line 24, delete "dynometer" and insert --dynamometer--.

In Column 4, Line 4, delete "A" and insert --A.--.

In Column 8, Line 63, delete "dynometer" and insert --dynamometer--.

In Column 9, Line 38, delete "Botulox" and insert --Botulax--.

In Column 9, Line 38, delete "(Medytox)" and insert --(Medytox),--.

In Column 9, Line 40, delete "Koreatox" and insert --Coretox--.

In Column 10, Line 25, delete "$10_{-2}$" and insert --$10^{-2}$--.

In Column 10, Line 26, delete "$10_{-2}$" and insert --$10^{-2}$--.

In Column 10, Line 27, delete "$10_{-2}$" and insert --$10^{-2}$--.

In Column 10, Line 52, delete "Botox" and insert --Botox.--.

In Column 10, Line 53, delete "Botox" and insert --Botox.--.

In Column 10, Line 54, delete "Botox" and insert --Botox.--.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,869,914 B2

In Column 10, Line 55, delete "Botox" and insert --Botox.--.

In Column 10, Line 56, delete "Botox" and insert --Botox.--.

In Column 10, Line 57, delete "Koreatox" and insert --Coretox--.

In Column 10, Line 58, delete "Botox" and insert --Botox.--.

In Column 13, Line 1, delete "dynometer" and insert --dynamometer--.

In Column 13, Line 49, delete "intermetarsal" and insert --intermetatarsal--.

In Column 13, Line 52, delete "intermetarsal" and insert --intermetatarsal--.

In Column 15, Line 2, delete "dynometer" and insert --dynamometer--.

In Column 15, Line 31 (approx.), delete "Bupivicaine" and insert --Bupivacaine--.

In Column 16, Line 14 (approx.), delete "INTJ." and insert --INJ.--.

In Column 16, Line 14 (approx.), delete "INTJ." and insert --INJ.--.

In Column 16, Line 31, delete "intermetarsal" and insert --intermetatarsal--.

In Column 16, Lines 45-46, delete "intermetarsal" and insert --intermetatarsal--.

In Column 16, Line 64, delete "intermetarsal" and insert --intermetatarsal--.

In Column 17, Line 16 (approx.), delete "intermetarsal" and insert --intermetatarsal--.

In Column 17, Line 67, delete "A]" and insert --A].--.

In Column 18, Line 32, delete "intermetarsal" and insert --intermetatarsal--.

In Column 18, Line 37 (approx.), delete "intermetarsal" and insert --intermetatarsal--.

In Column 18, Line 44, delete "intermetarsal" and insert --intermetatarsal--.

In Column 18, Line 49, delete "intermetarsal" and insert --intermetatarsal--.

In Column 18, Line 51, delete "intermetarsal" and insert --intermetatarsal--.

In Column 18, Lines 64-65, delete "intermetarsal" and insert --intermetatarsal--.

In Column 19, Line 5, delete "intermetarsal" and insert --intermetatarsal--.

CERTIFICATE OF CORRECTION (continued)
U.S. Pat. No. 10,869,914 B2

In Column 19, Line 10, delete "intermetarsal" and insert --intermetatarsal--.

In Column 19, Line 16, delete "intermetarsal" and insert --intermetatarsal--.

In Column 19, Line 21, delete "intermetarsal" and insert --intermetatarsal--.

In Column 19, Line 27, delete "intermetarsal" and insert --intermetatarsal--.

In Column 19, Line 32, delete "intermetarsal" and insert --intermetatarsal--.

In the Claims

In Column 20, Line 20 (approx.), Claim 2, delete "dynometer" and insert --dynamometer--.

In Column 20, Lines 45-46, Claim 8, delete "as the needle as the needle" and insert --as the needle--.